(12) United States Patent
Takahashi et al.

(10) Patent No.: US 7,723,524 B2
(45) Date of Patent: May 25, 2010

(54) 8-CYANOQUINOLONECARBOXYLIC ACID DERIVATIVE

(75) Inventors: Hisashi Takahashi, Tokyo (JP); Rie Miyauchi, Tokyo (JP); Makoto Takemura, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 1007 days.

(21) Appl. No.: 10/572,742

(22) PCT Filed: Sep. 29, 2004

(86) PCT No.: PCT/JP2004/014262

§ 371 (c)(1),
(2), (4) Date: Mar. 21, 2006

(87) PCT Pub. No.: WO2005/030752

PCT Pub. Date: Apr. 7, 2005

(65) Prior Publication Data

US 2008/0255190 A1 Oct. 16, 2008

(30) Foreign Application Priority Data

Sep. 29, 2003 (JP) .............................. 2003-336864

(51) Int. Cl.
C07D 215/38 (2006.01)
(52) U.S. Cl. ..................... 546/156; 514/313
(58) Field of Classification Search ................. 546/156; 514/313
See application file for complete search history.

(56) References Cited

U.S. PATENT DOCUMENTS

| | | | |
|---|---|---|---|
| 5,098,912 A | 3/1992 | Hayakawa et al. | |
| 5,476,950 A | 12/1995 | Hayakawa et al. | |
| 5,849,757 A | 12/1998 | Takemura et al. | |
| 6,121,285 A * | 9/2000 | Takemura et al. | 514/312 |
| 6,184,388 B1 * | 2/2001 | Takemura et al. | 548/566 |
| 6,448,266 B1 * | 9/2002 | Takemura et al. | 514/312 |
| 6,825,353 B2 * | 11/2004 | Saito et al. | 546/156 |
| 6,900,225 B2 | 5/2005 | Takemura et al. | |
| 7,176,313 B2 * | 2/2007 | Takemura et al. | 544/363 |
| 7,238,694 B2 * | 7/2007 | Ding et al. | 514/253.04 |
| 2004/0063754 A1 | 4/2004 | Takahashi et al. | |

FOREIGN PATENT DOCUMENTS

| | | |
|---|---|---|
| DE | 37 02 393 | 8/1988 |
| EP | 0 235 762 | 9/1987 |
| JP | 63-201170 | 8/1988 |
| JP | 2000-319261 | 11/2000 |
| WO | 96/00208 | 1/1996 |
| WO | 96/11194 | 4/1996 |
| WO | 96/23782 | 8/1996 |
| WO | 97/19072 | 5/1997 |
| WO | 97/31001 | 8/1997 |
| WO | 98/26779 | 6/1998 |
| WO | 98/52939 | 11/1998 |
| WO | 98/54169 | 12/1998 |
| WO | 01/62734 | 8/2001 |
| WO | 02/40478 | 5/2002 |

OTHER PUBLICATIONS

Brossi, Arnold et al., "1-Ethyl-7-[3-[(ethylamino) methyl)]-1-pyrrolidinyl] -6,8-difluoro-1,4-dihydro-4-oxo-3-quinoline-carboxylic Acid. New Quinolone Antibacterial with Potent Gram-Positive Activity", Journal of Medicinal Chemistry, vol. 29, No. 4, pp. 445-448, 1986.

Domagala, John M. et al., "Quinolone Antibacterials Containing the New 7-[3-(1-Aminoethyl)-1-pyrrolidinyl] Side Chain: The Effects of the 1-Aminoethyl Moiety and Its Stereochemical Configurations on Potency and in Vivo Efficacy", Journal of Medicinal Chemistry, vol. 36, No. 7, pp. 871-882, 1993.

Hagen, Susan E. et al., "Synthesis and Antibacterial Activity of New Quinolones Containing a 7-[3-(1-Amino-1-methylethyl)-1-pyrrolidinyl] Moiety. Gram-Positive Agents with Excellent Oral Activity and Low Side-Effect Potential", Journal of Medicinal Chemistry, vol. 37, No. 6, pp. 733-738, 1994.

Kimura, Youichi et al., "Synthesis and Structure-Activity Relationships of 7-[3-(1-Aminoalkyl) pyrrolidinyl]- and 7-[3-1-aminocycloalkyl] pyrrolidinyl]-quinolone Antibacterials[1]), Chem. Pharm. Bull., pp. 1442-1454, vol. 42, No. 7, 1994.

* cited by examiner

*Primary Examiner*—D. Margaret Seaman
(74) *Attorney, Agent, or Firm*—Oblon, Spivak, McClelland, Maier & Neustadt, L.L.P.

(57) ABSTRACT

To provide a quinolone antibacterial drug and a therapeutic agent for infectious diseases, which exhibit potent antibacterial activity on Gram-positive and Gram-negative bacteria and which is highly safe.

A compound represented by the following formula (1):

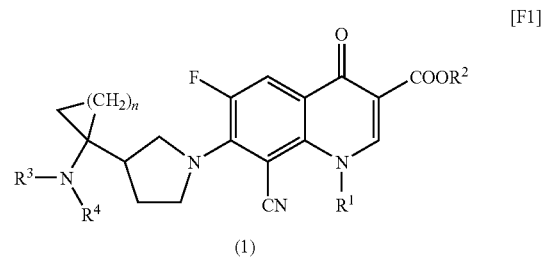

[F1]

(1)

(wherein $R^1$ represents a C3-C6 cycloalkyl group which may have a substituent or the like; $R^2$ represents a hydrogen atom or the like; $R^3$ and $R^4$ each independently represent a hydrogen atom or a C1-C6 alkyl group, or a substituted carboxyl group derived from an amino acid, a dipeptide, or a tripeptide, and, in the case where each of $R^3$ and $R^4$ represents a C1-C6 alkyl group, the alkyl group may be substituted by one or more atoms or groups selected from among a hydroxyl group, a halogen atom, a C1-C6 alkylthio group, and a C1-C6 alkoxy group; and n denotes an integer of 1 to 3), a salt thereof, and a hydrate of the compound or the salt. Also, antibacterial drugs and therapeutic agents for infectious diseases are prepared.

22 Claims, No Drawings

8-CYANOQUINOLONECARBOXYLIC ACID DERIVATIVE

TECHNICAL FIELD

The present invention relates to a quinolone compound which is useful as a pharmaceutical drug, a veterinary drug, a fishery drug or an antibacterial preservative, and further to an antibacterial agent and an antibacterial preparation which contain the compound as an active ingredient.

BACKGROUND ART

Since the discovery of norfloxacin, synthetic quinolone antibacterial agents have been significantly improved in terms of antibacterial activity and pharmacokinetics, and these agents have evolved into chemotherapeutic agents useful for treatment of systemic infectious diseases. Many of such synthetic quinolone compounds are currently used in clinical field.

In recent years, bacteria less susceptible to synthetic quinolone antibacterial agents have come to be increasingly developed in clinical field. For example, among Gram-positive bacteria, MRSA (methicillin-resistant *Staphylococcus Aureus*) and PRSP (penicillin-resistant *Streptococcus Pneumoniae*) in susceptible to β-lactam antibiotics, and VRE (vancomycin-resistant *Enterococcus*) in susceptible to an aminoglycoside antibacterial agent, a number of new types of bacteria that are resistant to drugs other than synthetic quinolone antibacterial agents and have low susceptibility to synthetic quinolone antibacterial agents is increasing. Therefore, there has been urgent need for development of a drug having higher efficacy in clinical field.

Apart from the above, it has become apparent that such synthetic antibacterial agents have various side effects such as convulsion which could occur when used in combination with a non-steroidal anti-inflammatory agent and phototoxicity. Therefore, development of a safer synthetic quinolone antibacterial agent is keenly demanded.

It has been known that antibacterial activity, pharmacokinetics, and safety of a synthetic quinolone antibacterial agent are influenced in large part with the structure of a substituent at the 7- or 1-position of the quinolone skeleton. Quinolone derivatives in which the 7-position of the quinolone skeleton is substituted by a 3-aminomethylpyrrolidinyl group are known to exhibit strong antibacterial activity on Gram-positive and Gram-negative bacteria. One example is a 7-[3-(1-aminomethyl)pyrrolidin-1-yl]quinolonecarboxylic acid derivative (see Non-Patent Document 1). Moreover, examples of quinolonecarboxylic acid derivatives derived from this specific quinolonecarboxylic acid derivative through substitution of the aminomethyl group include a 7-[3-(1-aminoethyl)pyrrolidin-1-yl]quinolonecarboxylic acid derivative (see Non-Patent Document 2), a 7-[3-(1-amino-1-methylethyl)pyrrolidin-1-yl]quinolonecarboxylic acid derivative (see Non-Patent Document 3), and a 7-[3-(1-aminoalkyl)pyrrolidin-1-yl]quinolonecarboxylic acid derivative (see Non-Patent Document 4).

However, most of the above-mentioned quinolonecarboxylic acid derivatives affect not only on bacteria but also on eukaryotic cells, because of low selective toxicity (see Non-Patent Document 5). Therefore, it is difficult for these derivatives to be used as pharmaceutical drugs or veterinary drugs. In fact, none of them have actually been used in clinical field so far.

Meanwhile, there are known quinolonecarboxylic derivatives related to the present invention such as compound (A) (see Patent Document 1) and compound (B) (see Patent Document 2) in which the 7-position of the quinolone skeleton is substituted by a 3-(1-aminocycloalkyl)pyrrolidinyl group. Note that the definitions of various substituents in compounds (A) (or (B)) are given in Patent Document 1 (or 2), and are not pertinent to the definitions provided in the present specification, even in cases where symbols are in common.

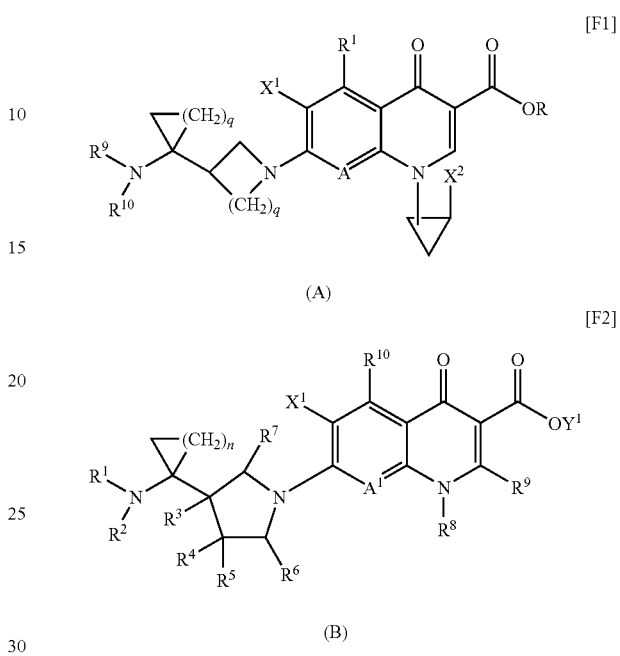

However, all the quinolonecarboxylic derivatives specifically disclosed in the above-mentioned applications have a common feature that the 8-position on the quinolone skeleton is substituted by a methyl group or a methoxy group, or that a methoxy group forms a ring with the nitrogen atom on the quinolone structure. These compounds exhibit relatively strong antibacterial activities as compared with conventional quinolone derivatives. However, they have strong acute toxicity and test positive in a micronucleus test, which is an indicative test for genetic toxicity.

Another known type of quinolonecarboxylic derivatives are quinolonecarboxylic derivatives (C) in which the 7- and 8-positions is substituted by a 3-(1-aminocycloalkyl)pyrrolidinyl group and a cyano group, respectively, and the 6-position is substituted only by a hydrogen atom (see Patent Document 3). Note that the definitions of various substituents in compound (C) are given in Patent Document 3, and such definitions are not pertinent to the definitions provided in the present specification, even in cases where symbols are in common.

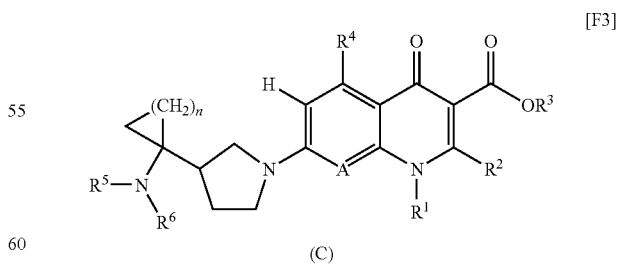

Furthermore, there are other quinolonecarboxylic derivatives disclosed so far, in which the 8- and 6-positions are substituted by a cyano group and a fluorine atom, respectively (see Patent Documents 4 to 8). However, compounds of this type do not have a 3-(1-aminocycloalkyl)pyrrolidinyl group at the 7-position.

Patent Document 1: International Publication WO 96/00208 pamphlet
Patent Document 2: International Publication WO 97/19072 pamphlet
Patent Document 3: International Publication WO 02/40478 pamphlet
Patent Document 4: European Patent No. 235762 specification
Patent Document 5: West Germany Patent No. 3702393 specification
Patent Document 6: International Publication WO 96/11194 pamphlet
Patent Document 7: International Publication WO 97/31001 pamphlet
Patent Document 8: International Publication WO 98/26779 pamphlet
Non-Patent Document 1: Journal of Medical Chemistry, Vol. 29, p. 445 (1986)
Non-Patent Document 2: Journal of Medical Chemistry, Vol. 36, p. 871 (1993)
Non-Patent Document 3: Journal of Medical Chemistry, Vol. 37, p. 733 (1994)
Non-Patent Document 4: Chemical & Pharmaceutical Bulletin, Vol. 42, p. 1442 (1994)

DISCLOSURE OF THE INVENTION

Problem to be Solved by the Invention

Accordingly, an object of the present invention is to provide a quinolone antibacterial agent and a quinolone therapeutic agent for infectious diseases, which exhibit potent antibacterial activity on Gram-positive and Gram-negative bacteria and are highly safe.

Means for Solving the Problem

In view of the foregoing, the present inventors conducted an extensive research in order to obtain a quinolone compound which exhibits excellent antibacterial activity and is highly safe, and eventually arrived at the findings that a 8-cyanoquinolonecarboxylic acid derivative represented by the following formula (1), a salt thereof, or a hydrate of the compound or the salt exhibits potent antibacterial activity on Gram-positive and Gram-negative bacteria, especially resistant bacteria such as Gram resistant Enterococci, including MRSA, PRSP, and VRE, as compared with known quinolone compounds, and is highly safe as an antibacterial agent. The present invention has been accomplished based on such findings.

Accordingly, the present invention provides a compound represented by the following formula (1):

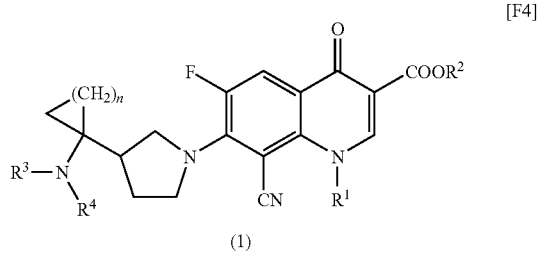

[F4]

(wherein $R^1$ represents a C1-C6 alkyl group, a C2-C6 alkenyl group, a C1-C6 halogenoalkyl group, a C3-C6 cycloalkyl group which may have a substituent, a C6-C20 aryl group which may have a substituent, a C3-C5 heteroaryl group which may have a substituent, a C1-C6 alkoxy group, or a C1-C6 alkylamino group; $R^2$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, a C1-C6 alkyl group, a C2-C7 alkoxymethyl group, or a phenylalkyl group composed of a C1-C6 alkylene group and a phenyl group; $R^3$ and $R^4$ each independently represent a hydrogen atom or a C1-C6 alkyl group, or a substituted carboxyl group derived from an amino acid, a dipeptide, or a tripeptide, and, in the case where each of $R^3$ and $R^4$ represent a C1-C6 alkyl group, the alkyl group may be substituted by one or more atoms or groups selected from among a hydroxyl group, a halogen atom, a C1-C6 alkylthio group, and a C1-C6 alkoxy group; and n denotes an integer of 1 to 3), a salt thereof, or a hydrate of the compound or the salt.

The present invention also provides compounds represented by the following formulas, salts thereof, or hydrates of the compounds or the salts.

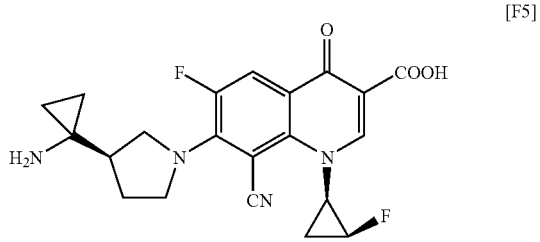

[F5]

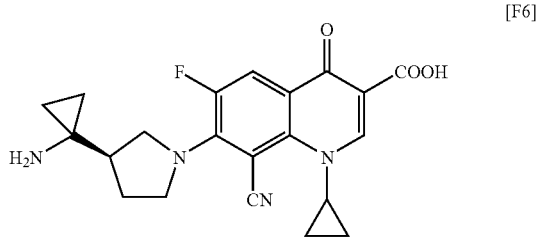

[F6]

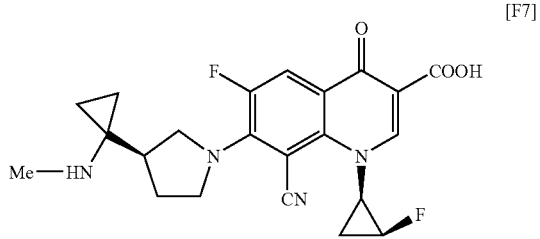

[F7]

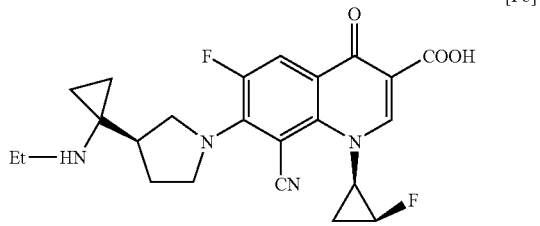

[F8]

-continued

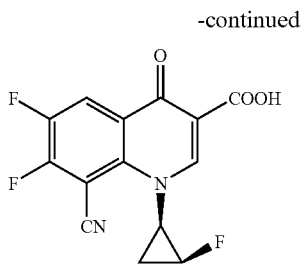

The present invention also provides a pharmaceutical drug, an antibacterial agent, and a therapeutic agent for an infectious disease, each containing, as an active ingredient, a compound represented by the above formula (1), a salt thereof, or a hydrate of the compound or the salt.

The present invention also provides a method for treating a disease characterized by comprising administering a compound represented by the above formula (1), a salt thereof, or a hydrate of the compound or the salt as an active ingredient; and a method for treating an infectious disease, characterized by comprising administering a compound represented by the above formula (1), a salt thereof, or a hydrate of the compound or the salt as an active ingredient.

The present invention also provides a method for producing a drug, characterized by incorporating, as an active ingredient, a compound represented by the above formula (1), a salt thereof, or a hydrate of the compound or the salt; a method for producing an antibacterial agent, characterized by comprising incorporating, as an active ingredient, a compound represented by the above formula (1), a salt thereof, or a hydrate of the compound or the salt; and a method for producing a therapeutic agent for an infectious disease, characterized by comprising incorporating, as an active ingredient, a compound represented by the above formula (1), a salt thereof, or a hydrate of the compound or the salt.

The present invention also provides use of a compound represented by the above formula (1), a salt thereof, or a hydrate of the compound or the salt for production of a drug; use of a compound represented by the above formula (1), a salt thereof, or a hydrate of the compound or the salt for production of an antibacterial agent; and use of a compound represented by the above formula (1), a salt thereof, or a hydrate of the compound or the salt for production of a therapeutic agent for an infectious disease.

ADVANTAGEOUS EFFECT OF THE INVENTION

The 8-cyanoquinolonecarboxylic acid derivative of the present invention exhibits exceptionally excellent antibacterial activity on Gram-positive and Gram-negative bacteria and high safety. Therefore, the 8-cyanoquinolonecarboxylic acid derivative of the invention is useful as an antibacterial agent and as a therapeutic agent for infectious diseases.

BEST MODE FOR CARRYING OUT THE INVENTION

Substituents on the compound of the present invention represented by the above formula (1) will next be described.

The C1-C6 alkyl group represented by $R^1$ is a C1-C6 linear or branched alkyl group. Specific examples include methyl, ethyl, propyl, isopropyl, butyl, isobutyl, sec-butyl, and tert-butyl, with ethyl being preferred. The C2-C6 alkenyl group is preferably vinyl or 1-isopropenyl. The C1-C6 halogenoalkyl group is a group corresponding to the above alkyl group which has been substituted by a halogen atom. Specific examples include fluoromethyl, 1-fluoroethyl, and 2-fluoroethyl, with 2-fluoroethyl being preferred.

Examples of the C3-C6 cycloalkyl group include cyclopropyl, cyclobutyl, and cyclopentyl, with cyclopropyl being preferred. The C3-C6 cycloalkyl group may have a substituent, and examples of the substituent include halogen atoms, the above alkyl groups, C1-C6 alkoxy (e.g., methoxy and ethoxy), cyano, nitro, amino, hydroxyl, and carboxyl, with halogen atoms being preferred. The C3-C6 cycloalkyl group which may have a substituent is preferably halogenocyclopropyl, more preferably fluorocyclopropyl. The halogenocyclopropyl is preferably monohalogenocyclopropyl. A cis-substituted form is more preferred.

Examples of the C6-C20 aryl group include phenyl and naphthyl, with phenyl being preferred. The C6-C20 aryl group may have a substituent, and examples of the substituent include those listed above in relation to the above cycloalkyl group. The number of the substituent is preferably 1 to 3. When the C6-C20 aryl group has a plurality of substituents, the substituents may be identical to or different from one another. Specifically, preferred are phenyl, 2-fluorophenyl, 4-fluorophenyl, 2,4-difluorophenyl, 2-fluoro-4-hydroxyphenyl, 3-amino-4,6-difluorophenyl, and 4,6-difluoro-3-methylaminophenyl.

The C3-C5 heteroaryl group is a 5- or 6-membered aromatic heterocyclic group having one or more hetero atoms selected from among S, N, and O. The aromatic heterocyclic group is preferably a 5- or 6-membered aromatic heterocyclic group having one or more N atoms. Specific examples include pyridyl, pyrimidyl, piperidinyl, pyrrolidinyl, morpholinyl, pyrrolyl, imidazolyl, pyrazolyl, pyridyl, pyrimidinyl, pyridazinyl, pyrrolidinyl, pyrrolinyl, imidazolidinyl, imidazolinyl, pyrazolidinyl, pyrazolinyl, piperidyl, and piperazinyl, with pyridyl being preferred. The aromatic heterocyclic group may have a substituent, and examples of the substituent include those listed above in relation to the above cycloalkyl group, with the above C1-C6 alkyl group, an amino group, and halogen atoms being preferred. The C3-C5 heteroaryl group which may have a substituent is preferably 6-amino-3, 5-difluoro-2-pyridyl.

Examples of the C1-C6 alkoxy group include methoxy, ethoxy, and propoxy, with methoxy being preferred.

The C1-C6 alkylamino group is an amino group which has been substituted by the above C1-C6 alkyl group. Specific examples include methylamino, ethylamino, and propylamino, with methylamino being preferred.

$R^1$ is preferably a non-substituted C3-C6 cycloalkyl group or a C3-C6 cycloalkyl group which has been substituted by a halogen atom.

Examples of $R^2$ include hydrogen, phenyl, acetoxymethyl, pivaloyloxymethyl, ethoxycarbonyl, choline, dimethylaminoethyl, 5-indanyl, phthalidinyl, 5-alkyl-2-oxo-1,3-dioxol-4-ylmethyl, 3-acetoxy-2-oxobutyl, the above C1-C6 alkyl group, C2-C7 alkoxymethyl, and phenylalkyl groups formed of a C1-C6 alkylene group and a phenyl group. The C2-C7 alkoxymethyl group is a methyl group which has been substituted by the above C1-C6 alkoxy group. Specific examples include methoxymethyl, ethoxymethyl, and propoxymethyl. Specific examples of the C1-C6 phenylalkyl group formed of an alkylene group and a phenyl group include phenylmethyl and phenylethyl. $R^2$ is preferably a hydrogen atom.

A quinolonecarboxylic acid derivative whose carboxylic acid moiety forms an ester is useful as a synthesis intermediate compound or a prodrug. Examples of an ester which is useful as a synthesis intermediate compound include alkyl esters, benzyl esters, alkoxyalkyl esters, phenylalkyl esters, and phenyl esters. Examples of an ester which is useful as a prodrug include esters that are readily cleaved in an organism to form a free carboxylic acid. Examples include acetoxymethyl ester, pivaloyloxymethyl ester, ethoxycarbonyl ester, choline ester, dimethylaminoethyl ester, 5-indanyl ester, phthalidinyl ester, 5-alkyl-2-oxo-1,3-dioxol-4-ylmethyl ester, and 3-acetoxy-2-oxobutyl ester.

$R^3$ and $R^4$ each independently represent a hydrogen atom or the above C1-C6 alkyl group, or a substituted carboxyl group derived from an amino acid, a dipeptide, or a tripeptide. When each of $R^3$ and $R^4$ represents the above C1-C6 alkyl group, the alkyl group may be substituted by one or more atoms or groups selected from among hydroxyl, halogen atoms, C1-C6 alkylthio group (e.g., methylthio, ethylthio, propylthio), and the above C1-C6 alkoxy group. Preferably, one of $R^3$ and $R^4$ is a hydrogen atom, and the other is a hydrogen atom, the above C1-C6 alkyl group (preferably, a methyl group), or a substituted carboxyl group derived from an amino acid, a dipeptide, or a tripeptide. More preferably, one of $R^3$ and $R^4$ is a hydrogen atom, and the other is a hydrogen atom or the above C1-C6 alkyl group. Particularly preferably, each of $R^3$ and $R^4$ is a hydrogen atom, or one of $R^3$ and $R^4$ is a hydrogen atom, and the other is a methyl group. A quinolonecarboxylic acid derivative in which one of $R^3$ and $R^4$ is a hydrogen atom and the other is a substituted carboxyl group derived from an amino acid, a dipeptide, or a tripeptide is particularly useful as a prodrug.

Examples of the amino acid, dipeptide, and tripeptide include those which can provide a free amine through easy cleavage, in an organism, of a peptide bond between the carboxyl group of the amino acid, dipeptide, or tripeptide and the amino group present at the 7-position of the quinolonecarboxylic acid derivative. Specifically, amino acid such as glycine, alanine, or aspartic acid; dipeptide such as glycine-glycine, glycine-alanine, or alanine-alanine; and tripeptide such as glycine-glycine-alanine or glycine-alanine-alanine are preferred.

A letter n denotes an integer of 1 to 3, preferably 1 or 2, more preferably 1. That is, a 3-membered ring is more preferred.

In the stereochemical environment of the halogenocyclopropyl group represented by $R^1$, the halogen atom and the quinolonecarboxylic acid moiety preferably are in the cis geometrical relationship with respect to the cyclopropane ring. There are two cis-substituents; i.e., 2-(S)-halogeno-1-(R)-cyclopropyl and 2-(R)-halogeno-1-(S)-cyclopropyl. Of these, the former is preferred.

The compound of the present invention exhibits excellent antibacterial activity, since the compound has a cyano group at the 8-position of the quinolone skeleton and a substituent represented by the following formula (D):

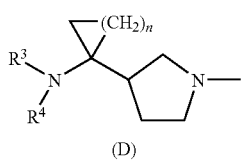

(D)

at the 7-position of the skeleton. The substituent has two optical isomers (represented by the following formulas (D1) and (D2)) which are antipodes to each other with respect to the asymmetric carbon atom at the 3-position of the pyrrolidine ring. As described in International Publication WO 02/40478 pamphlet, the 3R form is preferred.

[F11]

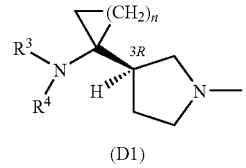 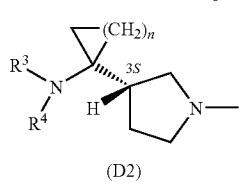

(D1) (D2)

When the compound of the present invention represented by the above formula (1) includes diastereomers, and when the compound of the present invention is administered to a human or an animal, the compound to be administered is preferably formed of a single diastereomer. The expression "formed of a single diastereomer" includes not only the case where the compound is exclusively composed of a single-type diastereomer, but also the case where the compound contains a diastereomer of the other type in such an amount that does not affect physical constants and activity. The expression "stereochemically pure" includes not only the case where, when a compound has optical isomers, the compound is exclusively composed of a single optical isomer, but also the case where the compound contains the other optical isomer in such an amount that does not affect physical constants and activity.

The compound (1) of the present invention may be of a free form. Alternatively, an acid addition salt or a salt with a carboxylic group may be formed. Examples of the acid addition salt include inorganic acid salts such as hydrochloride, sulfate, nitride, hydrobromide, hydriodate, and phosphate; and organic acid salts such as sulfonate (e.g., methanesulfonate, benzenesulfonate, p-toluenesulfonate), and carboxylate (e.g., acetate, citrate, maleate, fumarate, lactate). Examples of the salt with a carboxyl group include alkali metal salts such as lithium salt, sodium salt, and potassium salt; alkaline earth metal salts such as magnesium salt and calcium salt; ammonium salt, triethylamine salt, N-methylglucamine salt, and tris-(hydroxymethyl)aminomethane salt. The compound (1) of the present invention in free form and an acid addition salt or a salt with a carboxyl group of the compound (1) may be present as a hydrate.

Specific examples of the compound (1) of the present invention include:

7-[3-(R)-(1-aminocyclopropyl)pyrrolidin-1-yl]-8-cyano-6-fluoro-1-[2-(S)-fluoro-1-(R)-cyclopropyl]-1,4-dihydro-4-oxoquinoline-3-carboxylic acid, a salt thereof, or a hydrate of the carboxylic acid or the salt; 7-[3-(R)-(1-aminocyclopropyl)pyrrolidin-1-yl]-8-cyano-6-fluoro-1-cyclopropyl-1,4-dihydro-4-oxoquinoline-3-carboxylic acid, a salt thereof, or a hydrate of the carboxylic acid or the salt; 8-cyano-6-fluoro-1-[2-(S)-fluoro-1-(R)-cyclopropyl]-1,4-dihydro-7-[3-(R)-(1-methylaminocyclopropylpyrrolidin)-1-yl]-4-oxoquinoline-3-carboxylic acid, a salt thereof, or a hydrate of the carboxylic acid or the salt; and 8-cyano-6-fluoro-7-[3-(R)-(1-ethylaminocyclopropyl)pyrrolidin-1-yl]-1-[2-(S)-fluoro-1-(R)-cyclopropyl]-1,4-dihydro-4-oxoquinoline-3-carboxylic acid, a salt thereof, or a hydrate of the carboxylic acid or the salt.

A process for producing a novel compound which is important as an intermediate relating to the present invention; i.e., ethyl 8-cyano-6,7-difluoro-1-[2-(S)-fluoro-1-(R)-cyclopropyl]-1,4-dihydro-4-oxoquinoline-3-carbozylate (11), will next be described in detail. The method for producing the compound of the present invention is not limited to the process described below.

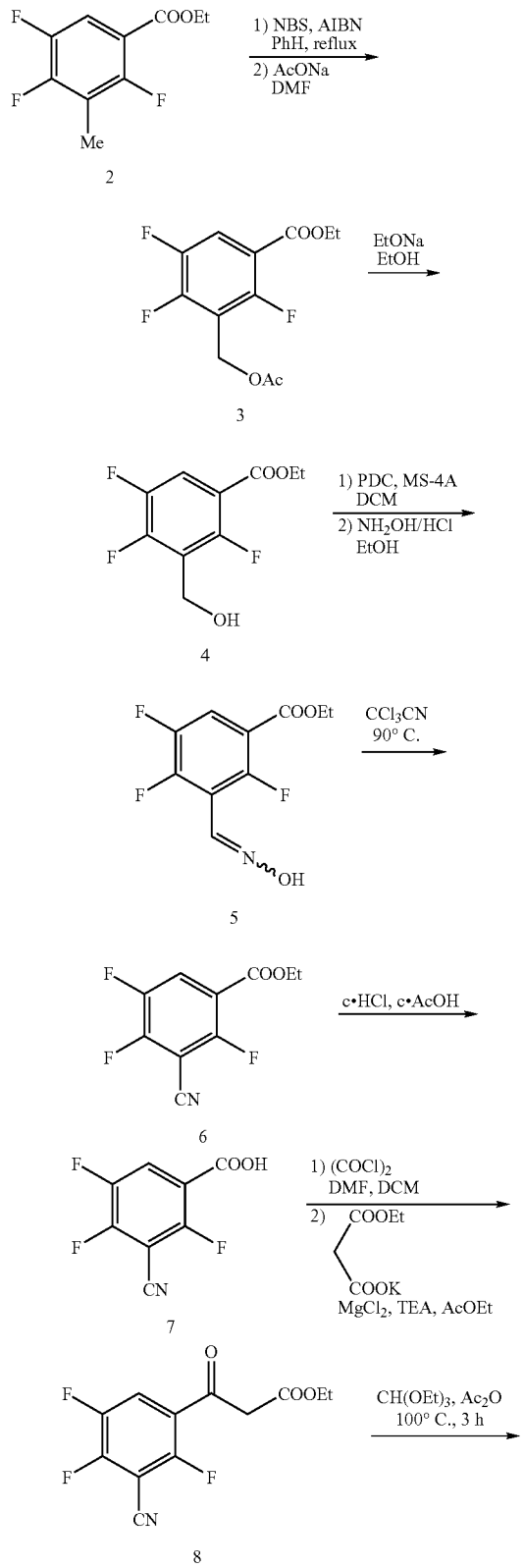

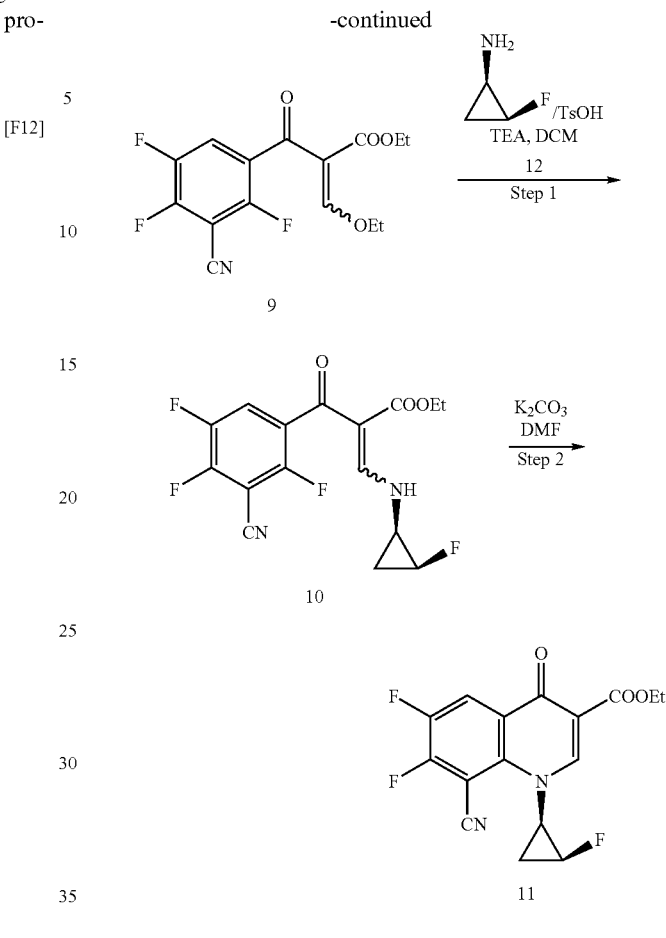

Step 1:

An intermediate compound (7) of a known compound (9) (the synthesis method is disclosed in, for example, European Patent No. 276,700 specification) may be produced through a method described in, for example, International Publication WO 98/47862 pamphlet. The compound (7) may be produced from a known compound (2) as described in the Referential Examples below. A novel compound ethyl 3-cyano-α-{[2-(S)-fluoro-1-(R)-cyclopropylamino]methylene}-2,4,5-trifluoro-β-oxobenzenepropanoate (10) may be produced by reacting the compound (9) with a compound (12) in a solvent and then carrying out an amine exchange reaction.

The compound (12) is composed of a cis-isomer alone, and may be produced through a method described in Japanese Patent Application Laid-Open (kokai) No. 2-231475. The compound (12) may be used in an amount of about 1 to about 1.2 equivalents with respect to the compound (9).

No particular limitation is imposed on the solvent which can be employed in step 1, so long as the solvent does not impede the reaction. Examples of the solvent include alcohol solvents such as methanol, ethanol, n-propanol, and n-cutanol; halogenated hydrocarbon solvents such as chloroform, methylene chloride, and dichloroethane; ether solvents such as tetrahydrofuran, diethyl ether, 1,4-dioxane, and dimethoxyethane; aromatic hydrocarbon solvents such as benzene, toluene, and xylene; and aprotic polar solvents such as acetonitrile, N,N-dimethylformamide, and dimethyl sulfoxide.

The reaction temperature is typically −60 to 50° C., preferably −20 to 30° C. The reaction time is 30 minutes to 48 hours, and the reaction is typically completed in about 30 minutes to about 4 hours.

When the compound (12) has formed a salt with an inorganic acid or an organic acid, in order to convert the compound (12) into a free amine, a base may be added to the reaction mixture in an amount of 1 to 1.5 equivalents or thereabouts. No particular limitation is imposed on the base, so long as the base does not impede the reaction. However, the base is preferably a tertially organic base. The tertially organic base is preferably trialkylamine, such as triethylamine.

The compound (10) may be isolated through a known method. However, depending on the solvent employed, the compound (10) may not be isolated and employed as itself in step 2.

Step 2:

For example, a novel compound ethyl 8-cyano-6,7-difluoro-1-[2-(S)-fluoro-1-(R)-cyclopropyl]-1,4-dihydro-4-oxoquinoline-3-carboxylate (11) may be produced through treatment of the compound (10) in a solvent in the presence of a base.

No particular limitation is imposed on the solvent which can be employed in step 2, so long as the solvent does not impede the reaction. Examples of the solvent include ether solvents such as tetrahydrofuran, diethyl ether, 1,4-dioxane, and dimethoxyethane; aromatic hydrocarbon solvents such as benzene, toluene, and xylene; aprotic polar solvents such as acetonitrile, N,N-dimethylformamide, and dimethyl sulfoxide, and a mixture of any suitable combination of these solvents.

Examples of the base which may be employed include potassium carbonate, socium hydride, and tert-butoxy potassium.

The reaction temperature is typically between ice cooling and 150° C., preferably 20 to 100° C. The reaction time is 30 minutes to 48 hours, and the reaction is typically completed in about 30 minutes to about 20 hours.

This reaction may employ a catalyst in accordance with needs. Examples of the catalyst include phase transfer catalysts such as Crown ether, tetrabutylammonium bromide, and benzyltriethylammonium bromide.

Steps 1 and 2 may be performed as a continuous reaction in a single common reaction container. After completion of reaction, the compound (11) is obtained through a method known per se. Specifically, an aqueous acidic solution such as hydrochloric acid is added dropwise to the reaction mixture to make the mixture weakly acidic, and the resultant mixture is extracted with a non-aqueous solvent, followed by concentration or removal of the solvent. Alternatively, the crystals that precipitate are collected through filtration. For further purification, a routine purification process such as column chromatography, recrystallization, or slurry heating may be employed to isolate the product as a pure product.

The compound (1) of the present invention may be produced from the compound (11) through, for example, the following process. Taking an exemplary compound referred to as Compound No. 1 described in the Examples section below, the production process will next be described.

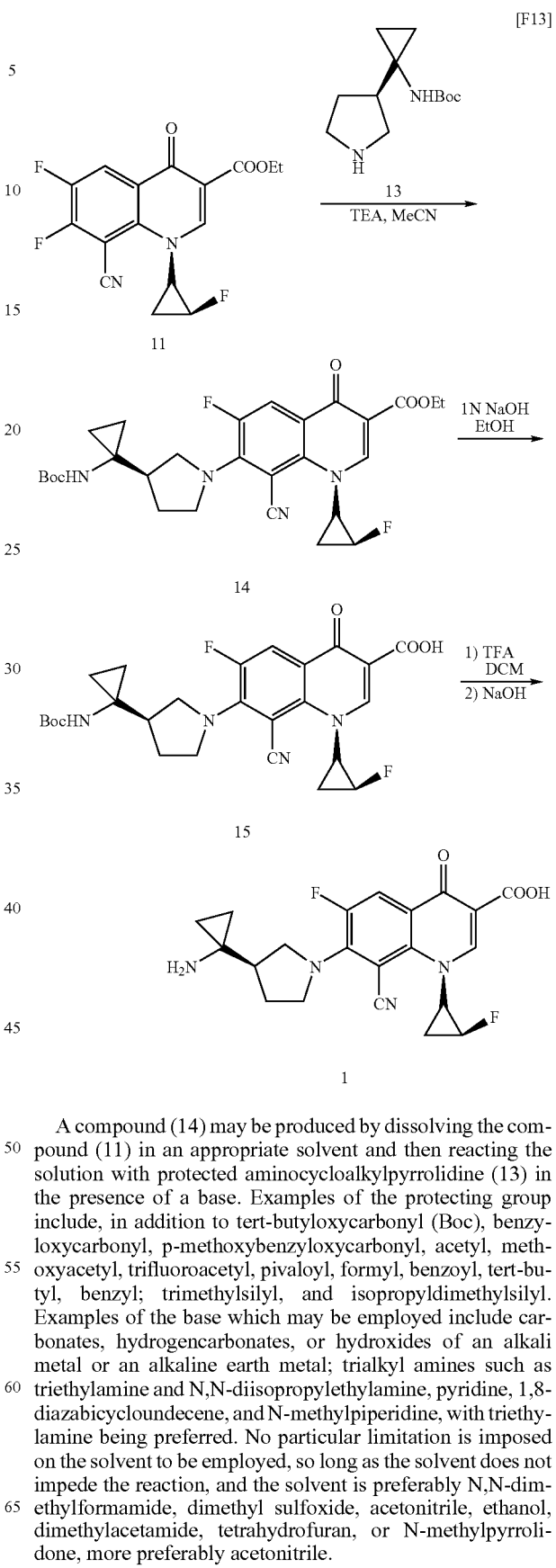

A compound (14) may be produced by dissolving the compound (11) in an appropriate solvent and then reacting the solution with protected aminocycloalkylpyrrolidine (13) in the presence of a base. Examples of the protecting group include, in addition to tert-butyloxycarbonyl (Boc), benzyloxycarbonyl, p-methoxybenzyloxycarbonyl, acetyl, methoxyacetyl, trifluoroacetyl, pivaloyl, formyl, benzoyl, tert-butyl, benzyl; trimethylsilyl, and isopropyldimethylsilyl. Examples of the base which may be employed include carbonates, hydrogencarbonates, or hydroxides of an alkali metal or an alkaline earth metal; trialkyl amines such as triethylamine and N,N-diisopropylethylamine, pyridine, 1,8-diazabicycloundecene, and N-methylpiperidine, with triethylamine being preferred. No particular limitation is imposed on the solvent to be employed, so long as the solvent does not impede the reaction, and the solvent is preferably N,N-dimethylformamide, dimethyl sulfoxide, acetonitrile, ethanol, dimethylacetamide, tetrahydrofuran, or N-methylpyrrolidone, more preferably acetonitrile.

Next, the compound (14) is hydrolyzed, and the protecting group of the amino group is removed, to thereby give the compound (1) of the present invention. Hydrolysis of the compound (14) may be performed under customary conditions. For example, the compound (14) may be reacted with a base in a solvent such as methanol or ethanol. The base is preferably sodium hydroxide. The reaction is preferably performed while cooling with ice. Deprotection may be performed under conditions which are suitable for the protecting group employed. For example, the compound (15) is dissolved in dichloromethane and then treated with trifluoroacetic acid while cooling with ice. After completion of reaction, the reaction mixture is made basic with aqueous sodium hydroxide.

The compound of the present invention has potent antibacterial activity and thus can be used as a drug for humans, animals, and fish or as a preservative for agricultural chemicals and food. When the compound of the present invention is used as a drug for humans, the daily dose for an adult is 50 mg to 1 g, preferably 100 to 500 mg. When the compound is used for veterinary purposes, the dose differs depending on the purpose of the administration, the size of the animal to be treated, the type of the pathogenic bacteria infecting the animal, and the severity of the infection. The daily dose is typically 1 to 200 mg, preferably 5 to 100 mg per kg (the weight of the animal). The daily dose is administered once a day, or 2 to 4 times a day in a divided manner. The daily dose may be increased in accordance with needs.

The compounds of the present invention are active on a broad range of microorganisms which cause various infectious diseases and thus are useful in treatment, prevention, or alleviation of pathological conditions caused by these pathogens. Examples of bacteria or bacteria-like microorganisms on which the compounds of the present invention exhibit efficacy include those belonging to the genus *Staphylococcus, Streptococcus pyogenes*, hemolytic *Streptococcus, Enterococcus, Streptococcus pneumoniae*, genus *Peptostreptococcus, Neisseria gonorrhoeae, Escherichia coli*, genus *Citrobacter*, genus *Schigella, Klebsiella pneumoniae*, genus *Enterobacter*, genus *Serratia*, genus *Proteus, Pseudomonas aeruginosa, Haemophilus influenzae*, genus *Acinetobacter*, genus *Campylobacter*, and *Chlamydia trachomatis*.

Examples of pathological conditions caused by these pathogens include folliculitis, furuncle, carbuncle, erysipelas, phelegmon, lymphangitis or lymphadenitis, panaritium, subcutaneous abscess, hidrosadenitis, aggregated acne, infectious atheroma, anal abscess, mastitis, superficial secondary infections caused by trauma, burn, operative wound, or similar wounds, laryngopharyngitis, acute bronchitis, tonsillitis, chronic bronchitis, bronchiectasis, diffuse panbronchiolitis, secondary infection caused by chronic respiratory diseases, pneumonia, pyelonephritis, cystitis, prostatitis, epididymitis, gonococcal urethritis, non-gonococcal urethritis, cholecystitis, cholangitis, bacillary dysentery, enteritis, uterine appendagitis, intrauterine infection, bartholinitis, tarsitis, hordeolum, dacryocystitis, tarsadenitis, corneal ulcer, otitis media, sinusitis, periodontitis, pericoronitis, gnathitis, peritonitis, endocarditis, sepsis, meningitis, and skin infectious diseases.

Examples of acid-fast bacteria on which the compounds of the present invention exhibit efficacy include members of the so-called *Mycobacterium tuberculosis* complex (*Mycobacterium tuberculosis, M. bovis, M. africanum*) and atypical acid-fast bacteria (*M. kansasii, M. marinum, M. scrofulaceum, M. avium, M. intracelluare, M. xenopi, M. fortuitum, M. chelonei*). Acid-fast bacterial infectious diseases caused by any of these pathogens are broadly categorized into three groups; i.e., tuberculosis, atypical acid-fast bacterial disease, and lepra, based on the identity of the causal bacterium. *Mycobacterium tuberculosis* can be seen not only in the lungs, but also in the thoracic cavity, trachea/bronchi, lymph nodes, systemically disseminated, bone joints, meninges or brain, digestive organs (intestine or liver), skin, mammary gland, eye, middle ear or throat, urinary tract, male genital organs, and female genital organs. Atypical acid-fast bacteriosis (nontuberculous mycobacteriosis) is primarily found in the lung, but also found in local lymphadenitis, skin soft tissue, bone joints, and systemic disseminated pathological condition.

The compounds of the present invention are effective on a variety of microorganisms which cause infectious disease in animals. Examples of such microorganisms include those belonging to the genus *Escherichia*, genus *Salmonella*, genus *Pasteurella*, genus *Haemophilus*, genus *Bordetella*, genus *Staphylcoccus*, and genus *Mycoplasma*. Specific examples of diseases include, in birds, *Escherichia coli* infections, pullorum disease, avian paratyphoid, fowl cholera, infectious coryza, staphylococcosis, and mycoplasmosis; in pigs, *Escherichia coli* infections, salmonellosis, pasteurellosis, *Haemophilus* infectious disease, atrophic rhinitis, exudative epidermitis, mycoplasmosis; in cattle, *Escherichia coli* infections, salmonellosis, hemorrhagic septicemia, mycoplasmosis, contagious bovine pleuropneumonia, and mastitis; in dogs, *Escherichia coli* infections, septicemia, *salmonella* infectious disease, hemorrhagic septicemia, uterine empyema, and cystitis; and in cats, exudative pleurisy, cystitis, chronic rhinitis, *haemophilus* infectious disease, kitten diarrhea, and mycoplasmosis.

Antibacterial drugs containing a compound of the present invention can be prepared by selecting a suitable drug form in accordance with the manner of administration and using any of ordinarily employed preparation methods. Examples of the form of the antibacterial drugs containing a compound of the present invention as a main component include tablets, powder, granules, capsules, solutions, syrups, elixirs, oil or aqueous suspensions. Injection drugs may contain a stabilizer, a preservative, or a solubilizing agent. Alternatively, a solution which may contain any of these additives may be placed in a container and converted into solid through, for example, freeze-drying, and the thus—prepared solid preparation may be restituted before use. In this connection, a single dose or a plurality of doses may be contained into one container. Exemplary external application forms include solutions, suspensions, emulsions, ointments, gels, creams, lotions, and sprays.

Solid preparations may contain pharmaceutically acceptable additives along with the active compound. Examples of such additives include fillers, binders, disintegrators, dissolution accelerators, humectants, and lubricants. Exemplary liquid preparation forms include solutions, suspensions, and emulsions, and they may contain as an additive a suspending agent, an emulsifier, or the like.

EXAMPLES

The present invention will next be described by way of Referential Examples and Examples, which should not be construed as limiting the invention thereto.

Referential Example 1

Ethyl 3-acetoxymethyl-2,4,5-trifluorobenzoate

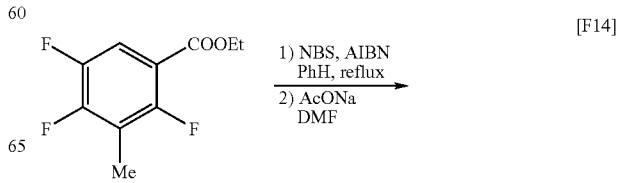

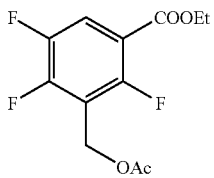

Ethyl 3-methyl-2,4,5-trifluorobenzoate (61.0 g, 279 mmol) was dissolved in benzene (1,000 mL). N-Bromosuccinimide (76.2 g, 428 mmol) and 2,2'-azobisisobutyronitrile (100 mg) were added thereto, and the mixture was refluxed for 3 days. The reaction mixture was left to cool, and the solid matter that precipitated was separated through filtration and washed with benzene. Subsequently, the filtrate and the wash solution were combined. The mixture was concentrated under reduced pressure. The residue was subjected to silica gel chromatography (eluent; n-hexane:ethyl acetate=20:1 to 10:1), to thereby yield a mixture of the starting material and ethyl 3-bromomethyl-2,4,5-trifluorobenzoate (about 1:1, 57.8 g). The mixture was dissolved in DMF (290 mL), and sodium acetate (22.1 g, 269 mmol) was added thereto, followed by stirring for 30 minutes at 90° C. The reaction mixture was left to cool, and ethyl acetate (1,000 mL) was added thereto. The mixture was washed with water (500 mL×2) and saturated brine (500 mL), and dried with sodium sulfate anhydrate. After filtration, the filtrate was concentrated under reduced pressure. The residue was subjected to silica gel chromatography (eluent; n-hexane:ethyl acetate=20:1), whereby the starting material was recovered in an amount of 27.4 g (45%) and the title compound was obtained as a pale yellow oily substance (26.5 g, 34%).

$^1$H-NMR (CDCl$_3$) δ ppm: 1.40 (3H, t, J=7.1 Hz), 2.09 (3H, s), 4.40 (2H, q, J=7.1 Hz), 5.22 (2H, t, J=1.5 Hz), 7.77-7.84 (1H, m).

Referential Example 2

Ethyl 3-hydroxyiminomethyl-2,4,5-trifluorobenzoate

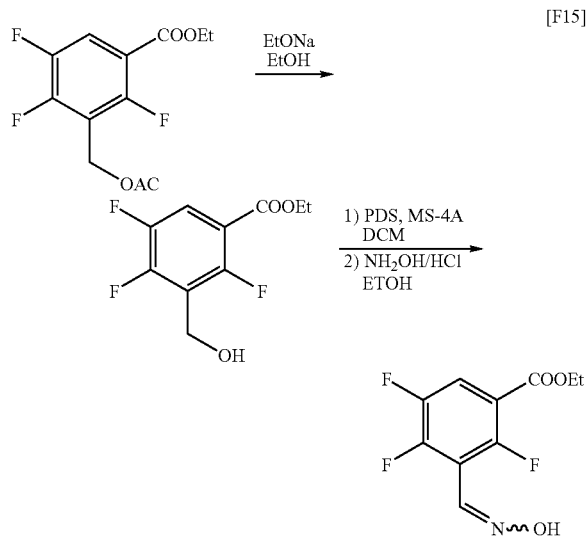

[F15]

Ethyl 3-acetoxymethyl-2,4,5-trifluorobenzoate (15.0 g, 54.2 mmol) was dissolved in ethanol (280 mL), and to the resultant solution, 21 wt % sodium ethoxide-ethanol solution (18.9 mL, 54.2 mmol) was added dropwise while cooling with ice. The resultant mixture was stirred at the same temperature for 10 minutes. While cooling with ice, saturated aqueous ammonium chloride (300 mL) was added to the reaction mixture and ethanol was concentrated under reduced pressure. The residual aqueous layer was extracted with ethyl acetate (300 mL×2). The organic layers were combined and washed with saturated brine (500 mL), followed by drying with sodium sulfate anhydrate. After filtration, the filtrate was concentrated under reduced pressure. The residue was dissolved in dichloromethane (50 mL), and while cooling with ice, the resultant solution was added dropwise to a suspension prepared through adding pyridinium dichromate (PDC) (40.2 g, 107 mmol) and Molecular Sieves 4A (40 g) to dichloromethane (150 mL). After completion of dropwise addition, the reaction mixture was stirred at room temperature for 16 hours, and diethyl ether (200 mL) and silica gel (40 g) were added thereto. The resultant mixture was concentrated under reduced pressure until the volume of the solvent was reduced to half. The solid matter that precipitated was separated through filtration and washed with diethyl ether. Subsequently, the filtrate and the wash solution were combined. The mixture was concentrated under reduced pressure. The residue was dissolved in ethanol (200 mL). Hydroxylamine hydrochloride (3.90 g, 56.1 mmol) was added to the resultant solution, and the mixture was stirred at 50° C. for 19 hours. The reaction mixture was concentrated under reduced pressure. The residue was dissolved in ethyl acetate (300 mL). The resultant solution was washed with water (300 mL) and saturated brine (300 mL), and dried with sodium sulfate anhydrate. After filtration, the filtrate was concentrated under reduced pressure. The residue was recrystallized from chloroform/n-hexane, to thereby yield the title compound as a white solid (12.2 g, 91%).

$^1$H-NMR (CDCl$_3$) δ ppm: 1.40 (3H, t, J=7.2 Hz), 4.37-4.44 (2H, m), 4.84 (1H, s), 7.73-7.84 (1H, m), 8.31 (1H, s).

Referential Example 3

Ethyl 3-cyano-2,4,5-trifluorobenzoate

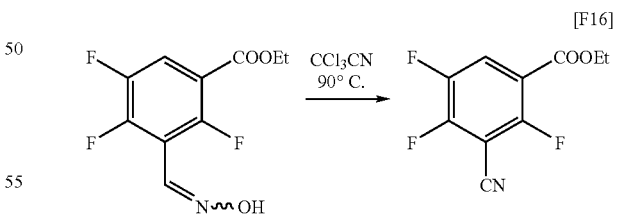

[F16]

Ethyl 3-hydroxyiminomethyl-2,4,5-trifluorobenzoate (5.5 g, 24.0 mmol) was dissolved in trichloroacetonitrile (25 g), and the solution was stirred at 90° C. for 16 hours. The reaction mixture was left to cool, and the solid matter that precipitated was separated through filtration. The filtrate was concentrated under reduced pressure. The residue was subjected to silica gel chromatography (eluent; n-hexane ethyl acetate=10:1), to thereby yield the title compound as a colorless oily substance (3.35 g, 61%).

$^1$H-NMR (CDCl$_3$) δ ppm: 1.41 (3H, t, J=7.1 Hz), 4.44 (2H, q, J=7.1 Hz), 8.07 (1H, td, J=9.3, 6.5 Hz).

Referential Example 4

3-Cyano-2,4,5-trifluorobenzoic acid

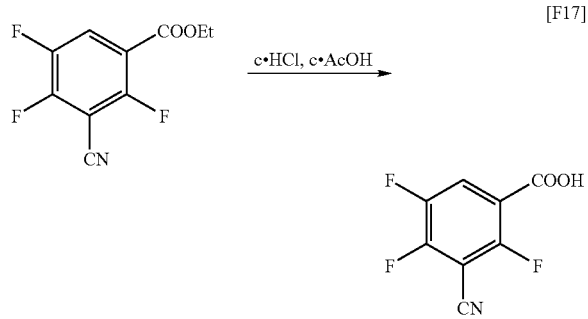

[F17]

Ethyl 3-cyano-2,4,5-trifluorobenzoate (3.35 g, 14.6 mmol) was suspended in glacial acetic acid (5 mL). Concentrated hydrochloric acid (10 mL) was added thereto, and the mixture was stirred at 100° C. for 4 hours. While cooling with ice, water (100 mL) was added to the reaction mixture. Subsequently, the resultant mixture was extracted with chloroform (100 mL×4), followed by drying with sodium sulfate anhydrate. After filtration, the filtrate was concentrated under reduced pressure. The residue was recrystallized from chloroform/n-hexane, to thereby yield the title compound as a white solid (2.86 g, 97%).

$^1$H-NMR (CDCl$_3$) δ ppm: 8.13 (1H, td, J=9.3, 6.6 Hz).

Referential Example 5

3-Cyano-2,4,5-trifluorobenzoylethyl acetate

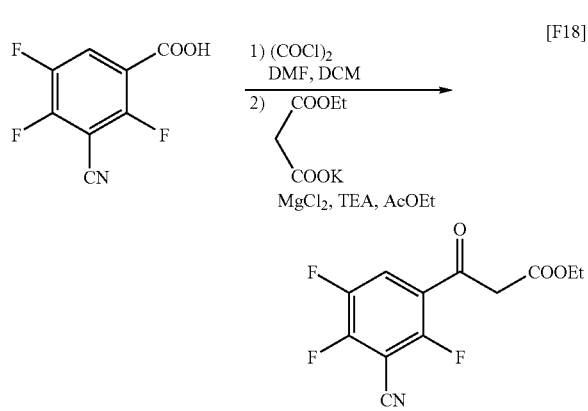

[F18]

The following reactions were performed in a nitrogen atmosphere. 3-Cyano-2,4,5-trifluorobenzoate (2.15 g, 10.7 mmol) was suspended in dichloromethane (22 mL). N,N-Dimethylformamide (5 drops) was added thereto, and oxalyl chloride (1.16 mL, 12.9 mmol) was added dropwise to the resultant mixture under stirring while cooling with ice. After completion of dropwise addition, the reaction mixture was stirred at room temperature (23 to 25° C.) for 5.5 hours. The reaction mixture was concentrated under reduced pressure, and co-boiled with toluene (5 mL×3), and the corresponding acid chloride was obtained as a concentration residue. Meanwhile, ethyl potassium malonate (3.74 g, 22.0 mmol), magnesium chloride (3.15 g, 33.0 mmol) and triethylamine (7.67 mL, 53.3 mmol) were added to ethyl acetate (55 mL), followed by stirring at 40° C. for 6 hours. To the mixture, the above-obtained acid chloride in dichloromethane (20 mL) was added under stirring while cooling with ice, and the resultant mixture was stirred at room temperature for 18 hours. The reaction mixture was cooled with ice, and 10% aqueous citric acid (100 mL) was added thereto. The mixture was stirred at room temperature for 10 minutes. The resultant mixture was extracted with ethyl acetate (100 mL×2). The organic layers were combined and washed sequentially with saturated sodium hydrogencarbonate (150 mL) and saturated brine (150 mL), followed by drying with sodium sulfate anhydrate. After filtration, the filtrate was concentrated under reduced pressure. The residue was subjected to silica gel chromatography (eluent; n-hexane:ethyl acetate=6:1), to thereby yield the title compound as a white solid (2.54 g, 88%).

$^1$H-NMR (CDCl$_3$) δ ppm: 1.28 (1.5H, t, J=7.1 Hz), 1.35 (1.5H, t, J=7.1 Hz), 3.97 (1H, d, J=3.9 Hz), 4.23 (1H, q, J=7.1 Hz), 4.30 (1H, q, J=7.1 Hz), 5.87 (0.5H, s), 7.98-8.11 (1H, m), 12.79 (0.5H, s).

Example 1

Ethyl 8-cyano-6,7-difluoro-1-[2-(S)-fluoro-1-(R)-cyclopropyl]-1,4-dihydro-4-oxoquinoline-3-carboxylate

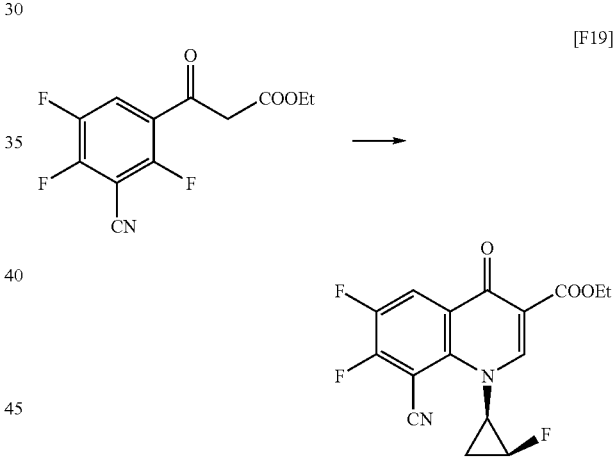

[F19]

3-Cyano-2,4,5-trifluorobenzoylethyl acetate (883 mg, 3.25 mmol) was dissolved in ethyl orthoformate (1.35 mL, 8.13 mmol). Acetic anhydride (1.07 mL, 11.4 mmol) was added thereto, and the resultant mixture was stirred at 100° C. for 5 hours. The reaction mixture was concentrated under reduced pressure and co-boiled with toluene (5 mL×3). The residue was dissolved in dichloromethane (20 mL). A 2-(S)-fluoro-1-(R)-cyclopropylamine p-toluenesulfonic acid salt (964 mg, 3.90 mmol) was added thereto, triethylamine (679 μL, 4.88 mmol) was added dropwise to the resultant mixture under stirring at −10° C. After completion of dropwise addition, the reaction mixture was stirred at room temperature for 17 hours. Subsequently, water (150 mL) was added to the reaction mixture, and the resultant mixture was extracted with ethyl acetate (150 mL×2). The organic layers were combined and washed with saturated brine (150 mL), followed by drying with sodium sulfate anhydrate. After filtration, the filtrate was concentrated under reduced pressure. The residue was dissolved in dimethylformamide (8 mL). Potassium carbonate (898 mg, 6.50 mmol) was added thereto under stirring while cooling with ice, and the resultant mixture was stirred at room temperature for 3 hours. The reaction mixture was cooled with ice, and 1N aqueous hydrochloric acid (15 mL) and water (30 mL) were added thereto, followed by stirring at room temperature for 2 hours. The solid matter that precipitated was collected through filtration and washed with water and a small amount of ethanol, to thereby yield the title compound as a pale yellow solid (890 mg, 82%).

$^1$H-NMR (CDCl$_3$) δ ppm: 1.41 (3H, t, J=7.1 Hz), 1.74 (1H, d, J=25.4 Hz), 1.86-1.97 (1H, m), 3.95-4.00 (1H, m), 4.41 (2H, q, J=7.1 Hz), 5.11 (1H, d, J=62.3 Hz), 8.55 (1H, dd, J=17.3, 8.5 Hz).

Example 2

7-[3-(R)-(1-Aminocyclopropyl)pyrrolidin-1-yl]-8-cyano-6-fluoro-1-[2-(S)-fluoro-1-(R)-cyclopropyl]-1,4-dihydro-4-oxoquinoline-3-carboxylate (Compound No. 1)

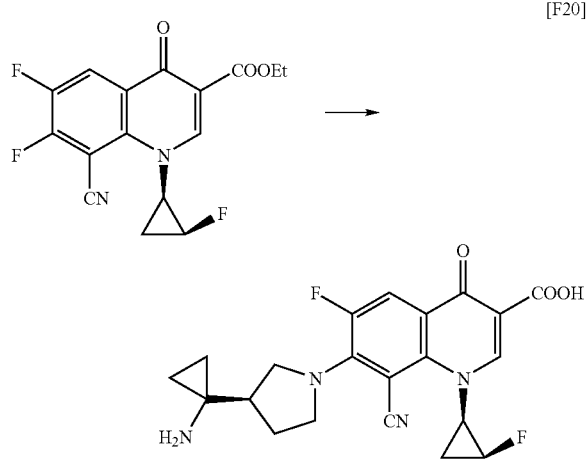

[F20]

3-(R)-[1-(tert-Butoxycarbonylamino)cyclopropyl]pyrrolidine (372 mg, purity: 80%, 1.32 mmol) and ethyl 8-cyano-6,7-difluoro-1-[2-(S)-fluoro-1-(R)-cyclopropyl]-1,4-dihydro-4-oxoquinoline-3-carboxylate (240 mg, 714 μmol) were added to acetonitrile (10 mL). Subsequently, triethylamine (185 μL, 1.33 mmol) was added thereto, and the resultant mixture was stirred in a nitrogen atmosphere for 4 hours. The reaction mixture was concentrated under reduced pressure. The residue was dissolved in chloroform (50 mL). The organic layer was washed with 10% aqueous citric acid (25 mL) and saturated brine (25 mL), and the organic layer was dried with sodium sulfate anhydrate. After filtration, the filtrate was concentrated under reduced pressure. Subsequently, while cooling with ice, 1 mol/L aqueous sodium hydroxide (1.43 mL) was added to the residue dissolved in ethanol (5 mL), followed by stirring at room temperature for 21 hours. 10% Aqueous citric acid (30 mL) was added to the reaction mixture to adjust the pH to 2 to 3, and the resultant mixture was extracted with chloroform (50 mL×4). The organic layer was washed with saturated brine (25 mL), and dried with sodium sulfate anhydrate. After filtration, the filtrate was concentrated under reduced pressure. The residue was dissolved in dichloromethane (2 mL). Trifluoroacetic acid (2 mL) was added dropwise thereto while cooling with ice, and the resultant mixture was stirred at room temperature for 3 hours. 1 mol/L Aqueous sodium hydroxide (10 mL) was added to the reaction mixture to adjust the pH to 12.0. Subsequently, hydrochloric acid was added to the resultant basic aqueous solution to adjust the pH to 7.4. The resultant mixture was extracted with chloroform (100 mL×5) and chloroform:methanol=9:1 (100 mL×2). The organic layer was dried with sodium sulfate anhydrate, and the solvent was removed under reduced pressure. The residue was recrystallized from methanol-isopropyl alcohol for purification, followed by drying under reduced pressure, to thereby yield the title compound as yellow crystals (206 mg, 70%).

$^1$H-NMR (400 MHz, 0.1N-NaOD) δ ppm: 0.57-0.60 (4H, m), 1.45 (1H, d, J=27.3 Hz), 1.66-1.80 (2H, m), 2.00-2.07 (1H, m), 2.15-2.24 (1H, m), 3.59-3.78 (3H, m), 3.91-4.04 (2H, m), 5.16 (1H, d, J=64.2 Hz) 7.75 (1H, d, J=15.6 Hz), 8.30 (1H, d, J=3.7 Hz).

IR (ATR) ν cm$^{-1}$: 3068, 2974, 2883, 2200, 1728, 1622, 1541, 1441, 1390, 1348, 1300, 1259.

Melting point: 138-140° C.

Elementary analysis: as $C_{21}H_{20}F_2N_4O_3 \cdot 0.5H_2O$

Calculated: C 59.57%; H 5.00%; N 13.23%

Found: C 59.37%; H 4.88%; N 13.04%

Example 3

7-[3-(R)-(1-Aminocyclopropyl)pyrrolidin-1-yl]-8-cyano-1-cyclopropyl-6-fluoro-1,4-dihydro-4-oxoquinoline-3-carboxylate (Compound No. 2)

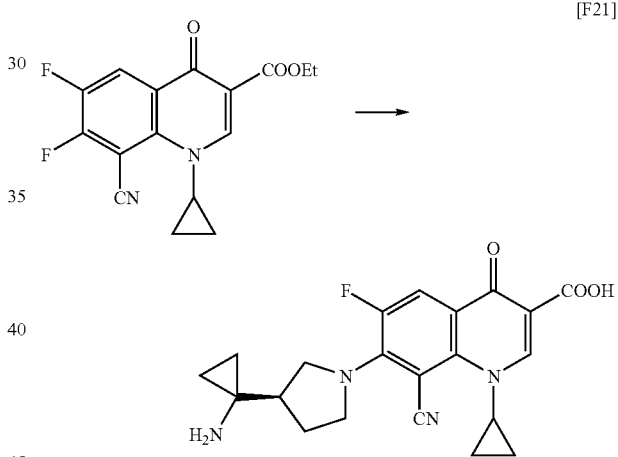

[F21]

3-(R)-[1-(tert-Butoxycarbonylamino)cyclopropyl]pyrrolidine (196 mg; purity: 80%, 693 μmol) and ethyl 8-cyano-1-cyclopropyl-6,7-difluoro-1,4-dihydro-4-oxoquinoline-3-carboxylate (170 mg, 534 μmol) were added to acetonitrile (4 mL). Subsequently, triethylamine (112 μL, 801 μmol) was added thereto, and the resultant mixture was stirred in a nitrogen atmosphere for 18 hours. The reaction mixture was concentrated under reduced pressure. The residue was dissolved in chloroform (50 mL). The organic layer was washed with 10% aqueous citric acid (25 mL) and saturated brine (25 mL), and the organic layer was dried with sodium sulfate anhydrate. After filtration, the filtrate was concentrated under reduced pressure. Subsequently, 1 mol/L aqueous sodium hydroxide (640 μL) was added to the residue dissolved in ethanol (5 mL) while cooling with ice, followed by stirring at room temperature for 19 hours. 10% Aqueous citric acid (10 mL) was added to the reaction mixture to adjust the pH to 2 to 3, and the resultant mixture was extracted with chloroform (50 mL×4). The organic layer was washed with saturated brine (25 mL), and dried with sodium sulfate anhydrate. After filtration, the filtrate was concentrated under reduced pressure. The residue was dissolved in dichloromethane (2 mL).

Trifluoroacetic acid (1 mL) was added dropwise thereto while cooling with ice, and the resultant mixture was stirred at room temperature for 2 hours. The solvent of the reaction mixture was removed under reduced pressure, and the residue was recrystallized from isopropyl alcohol for purification, followed by drying under reduced pressure, to thereby yield the title compound as yellow crystals (200 mg, 73%).

$^1$H-NMR (400 MHz, 0.1N-NaOD) δ ppm: 0.60 (4H, brs), 0.99 (1H, brs), 1.12-1.17 (1H, m), 1.26-1.31 (1H, m), 1.40-1.45 (1H, m), 1.73-1.81 (1H, m), 2.03-2.10 (1H, m), 2.19-2.26 (1H, m), 3.67-3.80 (3H, m), 3.98-4.03 (2H, m), 7.75 (1H, dd, J=15.6, 3.7 Hz), 8.42 (1H, s).

IR (ATR) ν cm$^{-1}$: 3057, 2951, 2895, 2204, 1720, 1672, 1622, 1543, 1462, 1448, 1400, 1350, 1317, 1263.

Melting point: 148-152° C.

Elementary analysis: as
$C_{21}H_{21}FN_4O_3$·monotrifluoroacetate·0.75$H_2O$
Calculated: C 52.72%; H 4.52%; N 10.69%
Found: C 52.59%; H 4.36%; N 10.65%

Example 4

8-Cyano-6-fluoro-1-[2-(S)-fluoro-1-(R)-cyclopropyl]-1,4-dihydro-7-[3-(R)-(1-methylaminocyclopropyl)pyrrolidin-1-yl]-4-oxoquinoline-3-carboxylate (Compound No. 3)

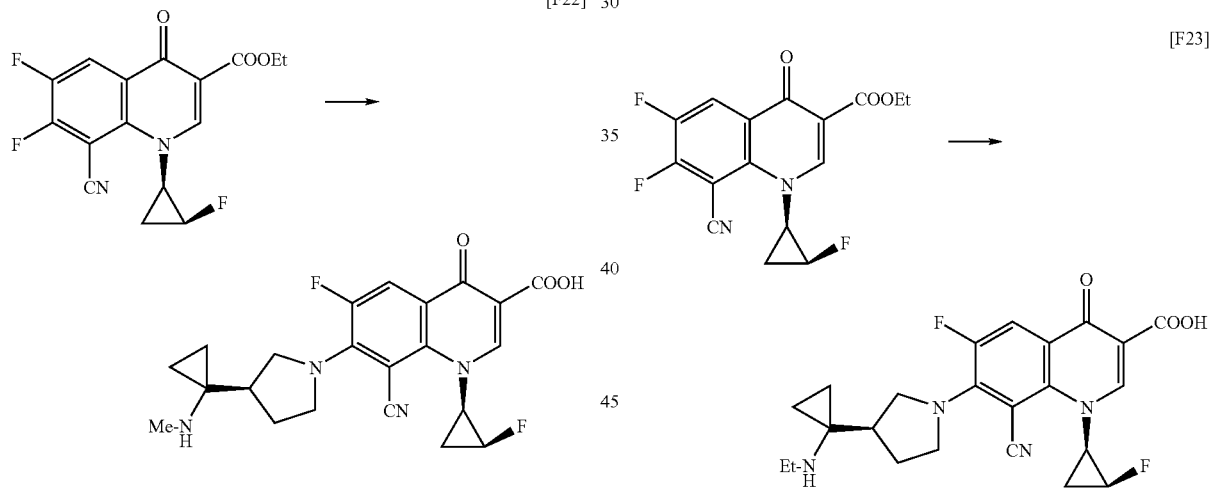

3-(R)-[1-(tert-Butoxycarbonylmethylamino)cyclopropyl]pyrrolidine (213 mg, 886 μmol) and ethyl 8-cyano-6,7-difluoro-1-[2-(S)-fluoro-1-(R)-cyclopropyl]-1,4-dihydro-4-oxoquinoline-3-carboxylate (248 mg, 738 μmol) were added to acetonitrile (6.0 mL). Subsequently, triethylamine (144 μL, 1.03 mmol) was added thereto, and the resultant mixture was stirred in a nitrogen atmosphere for 30 minutes. The reaction mixture was concentrated under reduced pressure. 1 mol/L Aqueous sodium hydroxide (2.95 mL) was added to the residue dissolved in ethanol (6 mL) while cooling with ice, followed by stirring at room temperature for 17 hours. Thereafter, 10% aqueous citric acid (25 mL) and water (25 mL) were added to the reaction mixture to adjust the pH to 2 to 3. The solid matter that precipitated was collected through filtration and washed with water (25 mL). The residue was dissolved in concentrated hydrochloric acid (5 mL) while cooling with ice, followed by washing with chloroform (50 mL×3). 10 mol/L Aqueous sodium hydroxide (6 mL) was added to the aqueous layer to adjust the pH to 12.0. Hydrochloric acid was added to the basic aqueous solution to adjust the pH to 7.4. The resultant mixture was extracted with chloroform (100 mL×3). The organic layer was dried with sodium sulfate anhydrate, and the solvent was removed under reduced pressure. The residue was purified through preparative chromatography, and further purified through recrystallization from isopropyl alcohol, then brought to dryness under reduced pressure, to thereby yield the title compound as pale yellow crystals (86.0 mg, 27%).

$^1$H-NMR (400 MHz, 0.1N-NaOD) δ ppm: 0.58-0.64 (4H, m), 1.41-1.55 (2H, m), 1.69-1.81 (1H, m), 1.97-2.04 (1H, m), 2.35 (3H, s), 2.84 (1H, brs), 3.59-3.72 (3H, m), 3.90-4.04 (2 μm), 5.16 (1H, d, J=67.9 Hz), 7.76 (1H, d, J=15.1 Hz), 8.30 (1H, d, J=3.9 Hz).

IR (ATR) ν cm$^{-1}$: 3332, 3066, 2945, 2885, 2794, 2197, 1726, 1624, 1541, 1441, 1375, 1350, 1300, 1259, 1232.

Melting point: 182-186° C.

Elementary analysis: as $C_{22}H_{22}F_2N_4O_3$·0.5$H_2O$
Calculated: C 60.41%; H 5.30%; F 8.69%; N 12.81%
Found: C 60.24%; H 5.42%; F 8.64%; N 12.34%

Example 5

8-Cyano-6-fluoro-7-[3-(R)-(1-ethylaminocyclopropyl)pyrrolidin-1-yl]-1-[2-(S)-fluoro-1-(R)-cyclopropyl]-1,4-dihydro-4-oxoquinoline-3-carboxylate (Compound No. 4)

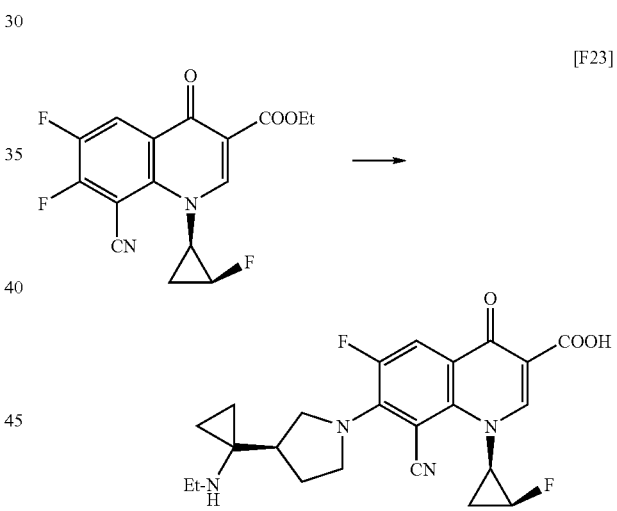

73%; N 11.91%

3-(R)-[1-(tert-Butoxycarbonylethylamino)cyclopropyl]pyrrolidine (259 mg, 1.02 mmol) and ethyl 8-cyano-6,7-difluoro-1-[2-(S)-fluoro-1-(R)-cyclopropyl]-1,4-dihydro-4-oxoquinoline-3-carboxylate (236 mg, 702 μmol) were added to acetonitrile (6.0 mL). Subsequently, triethylamine (144 μL, 1.03 mmol) was added thereto, and the resultant mixture was stirred in a nitrogen atmosphere for 30 minutes. The reaction mixture was concentrated under reduced pressure. 1 mol/L Aqueous sodium hydroxide (2.80 mL) was added to the residue dissolved in ethanol (6 mL) while cooling with ice, followed by stirring at room temperature for 17 hours. 10% Aqueous citric acid (25 mL) and water (25 mL) were added to the reaction mixture to adjust the pH to 2 to 3. The solid matter that precipitated was collected through filtration and washed with water (25 mL). The residue was dissolved in concentrated hydrochloric acid (5 mL) while cooling with ice, followed by washing with chloroform (50 mL×3). 10 mol/L Aqueous sodium hydroxide (6 mL) was added to the aqueous layer to adjust the pH to 12.0. Hydrochloric acid was added to the basic aqueous solution to adjust the pH to 7.4. The resultant mixture was extracted with chloroform (100 mL×3). The organic layer was dried with sodium sulfate anhydrate, and the solvent was removed under reduced pressure. The residue was recrystallized from isopropyl alcohol for purification, followed by drying under reduced pressure, to thereby yield the title compound as pale yellow crystals (89.9 mg, 27%).

$^1$H-NMR (400 MHz, 0.1N-NaOD) δ ppm: 0.58-0.65 (4H, m), 1.04-1.08 (3H, m), 1.43-1.54 (2H, m), 1.69-1.80 (1H, m), 2.00 (1H, brs), 2.71-2.75 (2H, m), 2.86 (1H, brs), 3.58-3.73 (3H, m), 3.90-4.05 (2H, m), 5.16 (1H, d, J=64.5 Hz), 7.77 (1H, d, J=15.1 Hz), 8.30 (1H, s).

IR (ATR) ν cm$^{-1}$: 3072, 2970, 2887, 2681, 2200, 1730, 1622, 1543, 1441, 1379, 1348, 1300, 1259, 1234.

Melting point: 133-137° C.

Elementary analysis: as $C_{23}H_{24}F_2N_4O_3 \cdot 1.75H_2O$
Calculated: C 58.28%; H 5.85%; F 8.02%; N 11.82%
Found: C 58.29%; H 5.53%; F 7.73%; N 11.91%

Test Example 1

Antibacterial activity of the compounds of the present invention was measured in accordance with the standard method designated by the Japanese Society of Chemotherapy. The results are shown in MIC values (µg/mL) (Table 1). For comparison with the MIC values of the compounds of the present invention, MIC values of levofloxacin (LVFX), ciprofloxacin (CPFX), and 7-[3-(R)-(1-aminocyclopropyl)pyrrolidin-1-yl]-8-cyano-1-[2-(S)-fluoro-1-(R)-cyclopropyl]-1,4-dihydro-4-oxoquinoline-3-carboxylic acid (control drug 1: represented by the following formula), which is described in International Publication WO 02/40478 pamphlet, are also shown in the table.

TABLE 2

| Bacteria/Compound | Control drug 1 | LVFX | CPFX |
| --- | --- | --- | --- |
| E. coli NIHJ | 0.012 | 0.012 | ≦0.003 |
| S. flexneri 2A 5503 | 0.012 | 0.025 | 0.006 |
| P. Vulgaris 08601 | 0.025 | 0.012 | ≦0.003 |
| K. pneumoniae TYPE I | 0.10 | 0.10 | 0.025 |
| S. marcescens 10100 | 0.10 | 0.10 | 0.025 |
| P. aeruginosa 32104 | 0.20 | 0.20 | 0.05 |
| P. aeruginosa 32121 | 0.10 | 0.10 | 0.025 |
| S. maltophilia IID 1275 | 0.78 | 0.39 | 0.78 |
| S. aureus FDA 209P | 0.006 | 0.20 | 0.10 |
| S. epidermidis 56500 | 0.05 | 0.39 | 0.20 |
| S. pyogenes G-36 | 0.025 | 0.78 | 1.56 |
| E. faevcalis ATCC 19433 | 0.10 | 0.78 | 0.78 |
| S. aureus 870307 | 0.39 | >6.25 | >6.25 |
| S. pneumoniae J24 | 0.025 | 0.78 | 0.39 |

As is clear from Tables 1 and 2, the compounds of the present invention exhibit very strong antibacterial activity which is effective against a broad range of Gram-positive and Gram-negative bacteria, including resistant bacteria.

Test Example 2

By use of compound Nos. 1 and 2, a mouse bone marrow micronucleus test was performed through the following method.

Groups of mice, each consisting of five, six-week-old, male Slc:ddY mice, were used. Compound Nos. 1 and 2 were dissolved in and diluted with 0.1 mol/L NaOH/saline. The medium; i.e., 0.1 mol/L NaOH/saline, was used as a control, and a drug solution which had been prepared by dissolving and diluting cyclophosphamide in saline was used as a positive control drug. All the drug solutions were disinfected through filtration by use of a Mylex GS 0.22 µm filter. Each drug solution was intravenously administered with a regimen of 10 mL/kg single dose at a rate of 0.2 mL/min (100 and 150

TABLE 1

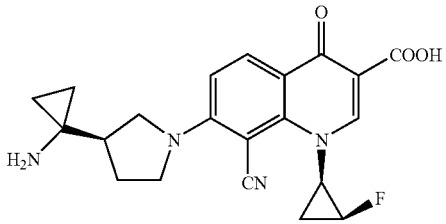

[F24]

| Bacteria/Compound | Compound No. 1 | Compound No. 2 | Compound No. 3 | Compound No. 4 |
| --- | --- | --- | --- | --- |
| E. coli NIHJ | ≦0.003 | ≦0.003 | ≦0.003 | 0.006 |
| S. flexneri 2A 5503 | ≦0.003 | ≦0.003 | ≦0.003 | 0.006 |
| P. Vulgaris 08601 | 0.006 | 0.006 | 0.012 | 0.012 |
| K. pneumoniae TYPE I | 0.025 | 0.012 | 0.025 | 0.025 |
| S. marcescens 10100 | 0.025 | 0.025 | 0.05 | 0.10 |
| P. aeruginosa 32104 | 0.10 | 0.10 | 0.10 | 0.20 |
| P. aeruginosa 32121 | 0.05 | 0.05 | 0.05 | 0.10 |
| S. maltophilia IID 1275 | 0.20 | 0.10 | 0.10 | 0.20 |
| S. aureus FDA 209P | ≦0.003 | ≦0.003 | 0.006 | 0.006 |
| S. epidermidis 56500 | 0.006 | 0.012 | 0.012 | 0.006 |
| S. pyogenes G-36 | 0.006 | 0.006 | 0.006 | 0.025 |
| E. faevcalis ATCC 19433 | 0.025 | 0.025 | 0.05 | 0.05 |
| S. aureus 870307 | 0.05 | 0.05 | 0.025 | 0.025 |
| S. pneumoniae J24 | 0.006 | 0.006 | 0.006 | 0.006 | mg/kg). Twenty four hours after administration, myeloma cells were collected from the femur bone, the smear preparations were prepared, and these were stained with acrylic orange. Under a fluorescence microscope, 1,000 polychromatic erythrocytes were observed for each individual mouse, and incidence of micronucleated polychromatic erythrocytes and the ratio of orthochromatic erythrocytes to polychromatic erythrocytes among 1,000 erythrocytes were calculated.

As a result, for Compound No. 1 of the present invention in particular, no significant difference in the micronucleus induction rate was observed between the control and the 150 mg/kg administration group, and the judgment result was thus negative. That is, Compound No. 1 of the present invention was found to be extremely weak in micronucleus induction; in other words, Compound No. 1 was found to be very safe.

The invention claimed is:

1. A compound represented by formula (1):

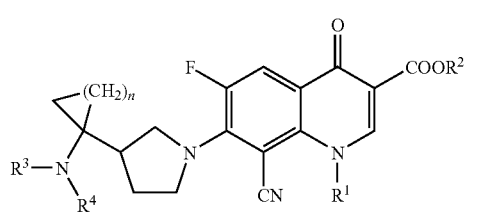

(1)

wherein $R^1$ represents a C1-C6 alkyl group, a C2-C6 alkenyl group, a C1-C6 halogenoalkyl group, a C3-C6 cycloalkyl group which may have a substituent, a C6-C20 aryl group which may have a substituent, a C3-C5 heteroaryl group which may have a substituent, a C1-C6 alkoxy group, or a C1-C6 alkylamino group; $R^2$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, a C1-C6 alkyl group, a C2-C7 alkoxymethyl group, or a phenylalkyl group formed of a C1-C6 alkylene group and a phenyl group; $R^3$ and $R^4$ each independently represent a hydrogen atom or a C1-C6 alkyl group, or a substituted carboxyl group derived from an amino acid, a dipeptide, or a tripeptide, and, in the case where each of $R^3$ and $R^1$ represents a C1-C6 alkyl group, the alkyl group may be substituted by one or more atoms or groups selected from among a hydroxyl group, a halogen atom, a C1-C6 alkylthio group, and a C1-C6 alkoxy group; and n denotes an integer of 1 to 3, or a salt thereof.

2. A compound according to claim 1, or a salt thereof, wherein the compound represented by formula (1) is stereochemically pure.

3. A compound according to claim 1, or a salt thereof, wherein the compound represented by formula (1) is stereochemically pure and represented by formula (2):

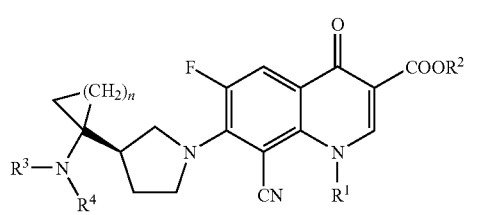

(2)

wherein $R^1$, $R^2$, $R^3$, $R^4$, and n are as defined above.

4. A compound according to claim 2, or a salt thereof wherein $R^1$ is a C3-C6 cycloalkyl group which may have a substituent.

5. A compound according to claim 4, wherein the C3-C6 cycloalkyl group which may have a substituent is a halogenocyclopropyl group.

6. A compound according to claim 5, or a salt thereof, wherein the halogenocyclopropyl group is a 1,2-cis-2-halogenocyclopropyl group.

7. A compound according to claim 6, or a salt thereof, wherein the 1,2-cis-2-halogenocyclopropyl group is a (1R, 2S)-2-halogenocyclopropyl group.

8. A compound according to claim 7 or a salt thereof, wherein the (1R,2S)-2-halogenocyclopropyl group is a (1R, 2S)-2-fluorocyclopropyl group.

9. A compound according to claim 1 or a salt thereof, wherein n is 1.

10. A compound according to claim 1, or a salt thereof, wherein one of $R^3$ and $R^4$ is a hydrogen atom, and the other is a substituted carboxyl group derived from an amino acid, a dipeptide, or a tripeptide.

11. A compound according to claim 1 or a salt thereof, wherein one of $R^3$ and $R^4$ is a hydrogen atom, and the other is a C1-C6 alkyl group.

12. A compound according to claim 1 or a salt thereof, wherein each of $R^3$ and $R^4$ is a hydrogen atom.

13. A compound according to claim 1 or a salt thereof, wherein $R^2$ is a hydrogen atom.

14. A compound represented by formula (3), or a salt thereof

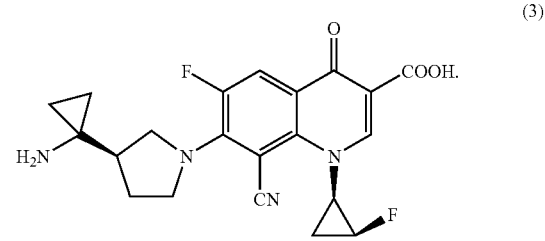

(3)

15. A compound represented by formula (4), or a salt thereof

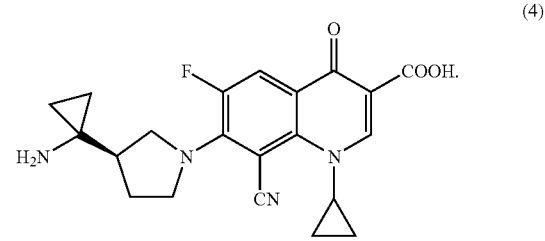

(4)

16. A compound represented by formula (5), or a salt thereof

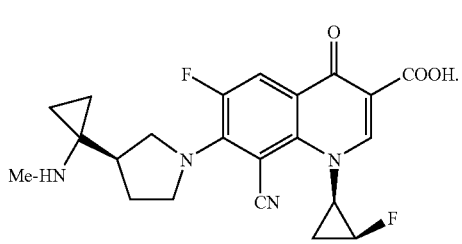

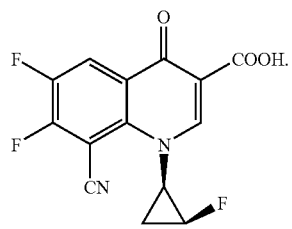

17. A compound represented by formula (6), or a salt thereof

18. A compound represented by formula (7), or a salt thereof

19. A compound according to claim 3, or a salt thereof, wherein $R^1$ is a C3-C6 cycloalkyl group which may have a substituent.

20. A method for treating a bacterial infection, comprising administering a compound according to any one of claims 1 to 17 or 19, a salt hereof, or a hydrate of the compound or the salt as an active ingredient.

21. A method of making a compositions comprising mixing a compound according to any one of claims 1 to 17 or 19, or a salt thereof with one or more pharmaceutically acceptable additives.

22. A composition comprising a compound according to any one of claims 1 to 17 or 19, or a salt thereof and one or more pharmaceutically acceptable additives.

* * * * *